(12) United States Patent
Sartor

(10) Patent No.: US 8,298,231 B2
(45) Date of Patent: Oct. 30, 2012

(54) BIPOLAR SCISSORS FOR ADENOID AND TONSIL REMOVAL

(75) Inventor: Joe D. Sartor, Longmont, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 816 days.

(21) Appl. No.: 12/359,692

(22) Filed: Jan. 26, 2009

(65) Prior Publication Data

US 2009/0198228 A1 Aug. 6, 2009

Related U.S. Application Data

(60) Provisional application No. 61/024,953, filed on Jan. 31, 2008.

(51) Int. Cl.
*A61B 18/04* (2006.01)
*A61B 18/18* (2006.01)

(52) U.S. Cl. ............................. 606/51; 606/33

(58) Field of Classification Search .............. 606/27–34, 606/40–52, 170–175, 205–211
See application file for complete search history.

(56) References Cited

U.S. PATENT DOCUMENTS

| | | | |
|---|---|---|---|
| 3,801,766 A | 4/1974 | Morrison, Jr. | |
| 3,935,405 A | 1/1976 | Auer | |
| 4,198,990 A | 4/1980 | Higgins et al. | |
| 4,488,873 A | 12/1984 | Bloomfield et al. | |
| 4,582,057 A | 4/1986 | Auth et al. | |
| 4,979,516 A | 12/1990 | Abraham, II | |
| 5,324,289 A | 6/1994 | Eggers | |
| 5,330,471 A | 7/1994 | Eggers | |
| 5,484,436 A | 1/1996 | Eggers et al. | |
| 5,540,685 A | 7/1996 | Parins et al. | |
| 5,658,322 A | 8/1997 | Fleming | |
| 5,720,742 A | 2/1998 | Zacharias | |
| 5,766,166 A | 6/1998 | Hooven | |
| 5,944,718 A * | 8/1999 | Austin et al. ................... | 606/48 |
| 6,090,108 A | 7/2000 | McBrayer et al. | |
| 6,142,992 A | 11/2000 | Cheng et al. | |
| 6,179,837 B1 | 1/2001 | Hooven | |
| 6,235,020 B1 | 5/2001 | Cheng et al. | |
| 6,296,636 B1 | 10/2001 | Cheng et al. | |
| 6,306,134 B1 | 10/2001 | Goble et al. | |
| 6,312,430 B1 * | 11/2001 | Wilson et al. ................... | 606/50 |
| 6,464,701 B1 * | 10/2002 | Hooven et al. ................. | 606/50 |
| 6,620,189 B1 | 9/2003 | Machold et al. | |
| 6,766,794 B1 | 7/2004 | Bently | |
| 6,837,888 B2 | 1/2005 | Ciarrocca et al. | |

(Continued)

FOREIGN PATENT DOCUMENTS

DE 179607 3/1905

(Continued)

OTHER PUBLICATIONS

European Search Report for EP 09 15 1738 dated Jun. 30, 2009.

(Continued)

*Primary Examiner* — Matthew F DeSanto

(57) ABSTRACT

A bipolar electrosurgical instrument is disclosed for use in excising tissues. The disclosed bipolar electrosurgical instrument includes a pair of jaws or legs having shearing surfaces, one of which is electrically nonconductive. The disclosed bipolar surgical instrument also includes conductive surfaces on the legs which allow energy flux to flow through tissue on a plane other than that defined by the relative shearing surfaces.

20 Claims, 7 Drawing Sheets

U.S. PATENT DOCUMENTS

| | | | |
|---|---|---|---|
| 6,842,692 B2 | 1/2005 | Fehr et al. | |
| 6,941,952 B1 | 9/2005 | Rush, III | |
| 6,974,453 B2 | 12/2005 | Woloszko et al. | |
| 7,033,356 B2* | 4/2006 | Latterell et al. | 606/48 |
| 7,285,117 B2 | 10/2007 | Krueger et al. | |
| 7,375,880 B2 | 5/2008 | Nakamura | |
| 7,918,848 B2* | 4/2011 | Lau et al. | 606/29 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 390937 | 10/1990 |
| EP | 556705 | 8/1993 |
| EP | 608609 | 8/1994 |
| EP | 0 517 244 | 3/1996 |
| EP | 836868 | 4/1998 |
| EP | 1051948 | 11/2000 |
| EP | 880220 | 6/2006 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 | 8/2001 |
| SU | 166452 | 1/1965 |
| SU | 727201 | 4/1980 |
| WO | WO 96/22740 | 8/1996 |
| WO | WO 2004/039416 | 5/2004 |

OTHER PUBLICATIONS

U.S. Appl. No. 12/057,557, filed Mar. 28, 2008.
U.S. Appl. No. 10/406,690, filed Apr. 3, 2003.
U.S. Appl. No. 11/242,458, filed Oct. 3, 2005.
U.S. Appl. No. 10/573,713, filed Mar. 28, 2006.
U.S. Appl. No. 12/136,620, filed Jun. 10, 2008.
U.S. Appl. No. 12/389,168, filed Feb. 19, 2009.
U.S. Appl. No. 12/351,935, filed Jan. 12, 2009.
U.S. Appl. No. 12/401,981, filed Mar. 11, 2009.
U.S. Appl. No. 12/351,947, filed Jan. 12, 2009.
U.S. Appl. No. 12/407,896, filed Mar. 20, 2009.
U.S. Appl. No. 12/205,525, filed Sep. 5, 2008.
U.S. Appl. No. 12/249,263, filed Oct. 10, 2008.
U.S. Appl. No. 12/249,218, filed Oct. 10, 2008.
U.S. Appl. No. 12/351,970, filed Jan. 12, 2009.
U.S. Appl. No. 12/351,960, filed Jan. 12, 2009.
U.S. Appl. No. 12/205,298, filed Sep. 5, 2008.
U.S. Appl. No. 12/351,980, filed Jan. 12, 2009.
U.S. Appl. No. 12/203,734, filed Sep. 3, 2008.
U.S. Appl. No. 12/242,102, filed Sep. 30, 2008.
U.S. Appl. No. 12/241,861, filed Sep. 30, 2008.
U.S. Appl. No. 12/242,061, filed Sep. 30, 2008.
U.S. Appl. No. 12/242,026, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04015981.6 dated Sep. 29, 2004.
International Search Report EP04707738 dated Jul. 4, 2007.

International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.

* cited by examiner

BIPOLAR SCISSORS FOR ADENOID AND TONSIL REMOVAL

CROSS-REFERENCE TO RELATED APPLICATIONS

This application claims the benefit of priority to U.S. Provisional Application Ser. No. 61/024,953 entitled "BIPOLAR SCISSORS FOR ADENOID AND TONSIL REMOVAL" filed Jan. 31, 2008 by Joe D. Sartor, which is incorporated by reference herein.

BACKGROUND

1. Technical Field

The present disclosure relates to electrosurgical scissors. More particularly, the present disclosure relates to a bipolar scissors for adenoid and tonsil removal.

2. Background of Related Art

Surgical scissors are commonly used in many surgical procedures for cutting tissue that is vascularized, i.e. contains blood or other vessels. The resultant bleeding or other fluid loss that occurs is not only of concern from the standpoint of fluid loss, but blood may also obscure the surgical field or site. Controlling such fluid loss and bleeding has, in the past, required significant time and attention of the surgeon during many procedures.

Scissors that use radiofrequency (RF) energy in a manner such that the tissue is heated as it is cut, thus promoting immediate hemostasis, have been used for many years to control such bleeding or other fluid loss. Early electric surgical scissors used monopolar RF power, where the scissors constituted one electrode and the patient rested on the other electrode (which was typically in the form of a conductive mat) to complete the circuit. Current flowed generally through the patient between the electrodes due to the voltage applied across the electrodes by an RF power supply. The uncertainty of the path of current flow through the body and possible unintentional harm to other tissues, however, encouraged further development in electrosurgical scissors.

Recently, efforts have been made to develop electrosurgical scissors, as illustrated, for example, in U.S. Pat. Nos. 5,324,289 and 5,330,471, in which one blade includes one electrode and the other blade includes or functions as the other electrode, so the current flows between the blades as they cut the desired tissue.

More recently, electrosurgical scissors have been provided in which each cutting blade itself includes two electrodes for connection to a RF power supply. The tissue contacting surfaces of at least one, and typically both, include two spaced apart electrodes that extend along the tissue contacting surface and are connectable to a voltage supply for applying a voltage between the electrodes of each blade. As a result, current flows between the first and second electrodes of each blade to promote hemostasis in the tissue as the blade is moved into contact with the tissue, such as during the cutting action. Such scissors are disclosed in U.S. Pat. Nos. 6,179,837 and 5,766,166. Another example of electrosurgical scissors is disclosed in U.S. Pat. No. 5,540,685.

In certain applications, such as, for example, removal of adenoid or tonsils, it is desirable to be able to control the application of current across the tissue so as to control the timing of the hemostasis as the tissues are cut. Polyps are abnormal tissue growths generally projecting away from mucosal tissues. Tonsils are naturally occurring lymphatic structures in the pharynx that often need to be removed due to recurrent infection or airway occlusion. Often, they need to be removed by cutting them away from the underlying tissue and cauterizing the tissue to prevent unnecessary bleeding. In certain instances, it is desirable to cauterize them and initiate hemostasis during the initial cutting, suspend hemostasis as the tissue is being cut, and resume hemostasis towards the end of the excising procedure.

SUMMARY

There is provided an electrosurgical instrument for cutting tissue. In one embodiment, the electrosurgical instrument generally includes a first leg having a first electrically conductive portion which forms a first shearing surface and a first side surface the electrosurgical instrument further includes a second leg which is movably mounted relative to the first leg between an open position and a closed position. The second leg includes a second electrically conductive portion and an electrically insulated portion. The electrically insulated portion forms a second shearing surface. The first shearing surface cooperates with the second shearing surface to cut tissue. In one embodiment, the first side surface of the first electrically conductive portion lies along a common plane with the first electrically conductive surface of the second electrically conductive portion. The second electrically conductive surface of the second electrically conductive portion is a bulbous surface projecting beyond the second shearing surface.

The second electrically conductive portion includes a first electrically conductive surface and a second electrically conductive surface insulated from the first electrically conductive surface. The second electrically conductive surface is in electrical communication with the first side surface when the first and second legs are in the closed position. The first electrically conductive surface is electrical communication with the first electrically conductive portion as the first leg is moved towards the second leg to cut tissue.

In one embodiment, the first leg includes an electrically insulated outer surface surrounding said first electrically conductive portion and the second leg includes an electrically insulated outer surface surrounding the second electrically conductive portion.

In one embodiment, the first and second legs are pivotally mounted for movement at a pin such that the pin electrically isolates the first leg from the second leg. The first leg has a first arm extending proximally from the pin and the second leg has a second arm extending proximally from the pin. At least one of the first and second arms has a fingering at a proximal end thereof to facilitate use by the user. The first and second arms each have an electrical connection at the proximal ends thereof for connection to electrical power source.

In one embodiment, the electrical power source is a radiofrequency (RF) power source.

In one embodiment the second shearing surface is formed of a ceramic material.

There is also disclosed an embodiment of an electrosurgical instrument for cutting and coagulating tissue which generally includes a first leg having a first electrically conductive portion forming a first shearing surface and a first side surface. The electrosurgical instrument also includes a second leg movably mounted relative to the first leg between an open position and a closed position. The first and second legs are pivotally mounted for movement at a pin, the pin electrically isolating the first leg from the second leg. The first leg has a first arm extending proximally from the pin and the second leg as a second arm extending proximally from the pin. The second leg includes a second electrically conductive portion and an electrically insulated portion. The electrically insulated portion forms a second shearing surface relative to the first shearing surface. The second electrically conductive portion includes a first electrically conductive surface and a second electrically conductive surface insulated from the first electrically conductive surface.

In one embodiment, the first side surface is in electrical communication with the second electrically conductive surface as the first and second legs are moved towards the closed position. The second electrically conductive surface of the second electrically conductive portion is a bulbous surface projecting beyond the second shearing surface.

In one embodiment, a least one of the first and second arms has a finger ring at a proximal end thereof.

The present disclosure also relates to a method for performing a surgical function. The method includes providing an electrosurgical instrument, positioning the electrosurgical instrument adjacent target tissue and moving a first leg or a second leg of the electrosurgical instrument toward the other to sever the target tissue therebetween. The first leg includes a first electrically conductive portion with a first shearing surface and a first side surface. The second leg is movably mounted relative to the first leg between an open position and a closed position and includes a second electrically conductive portion and a second shearing surface. The second electrically conductive portion includes a second electrically conductive surface that projects beyond the second shearing surface.

DESCRIPTION OF THE DRAWINGS

An embodiment of the presently disclosed bipolar scissors is disclosed herein with reference to the drawings, wherein.

DETAILED DESCRIPTION OF EMBODIMENTS

An embodiment of the presently disclosed electrosurgical instrument or bipolar scissors will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component farther away from the user.

Figure 1:
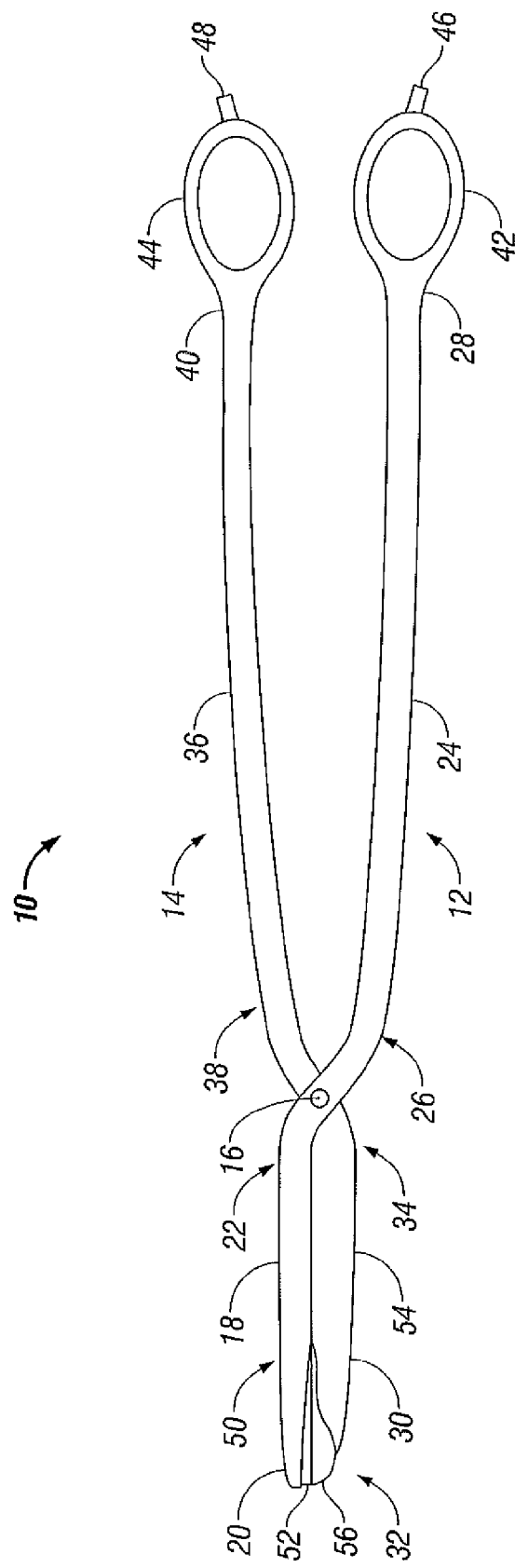
FIG. 1 is a side view of an embodiment of the disclosed bipolar scissors.

Referring initially to FIG. 1, there is disclosed a bipolar surgical instrument or bipolar scissors 10 that is particularly useful in excising adenoids or tonsils. Bipolar scissors 10 generally includes a first scissors half 12 and a second scissors half 14. First scissors half 12 and second scissors half 14 are pivotally connected together at a nonconductive pin 16 which electrically isolates first scissors half 12 from second scissors half 14. First scissors half 12 generally includes a first jaw or leg 18 having a distal end 20 and a proximal end 22. First scissors half 12 also includes a first arm 24 having a distal end 26 and a proximal end 28. Proximal end 22 of first leg 18 is integrally formed with distal end 26 of first arm 24 such that first scissors half 12 forms a general "S" shape at pin 16.

Similarly, second scissors half 14 includes a second jaw or leg 30 having a distal end 32 and a proximal end 34. Second scissors half 14 also includes a second arm 36 having a distal end 38 and a proximal end 40. Like first scissors half 12, proximal end 34 of second leg 30 is integrally formed with distal end 38 of second arm 36 and crosses at pin 16 in a generally "S" configuration. Thus, as proximal ends 28 and 40 are separated, first leg 18 and second leg 30 are moved apart to an open position spaced apart from each other. As proximal ends 28 and 40 are moved towards each other, first leg 18 and second leg 30 move to a closed cutting position. A first and a second finger ring, 42 and 44 respectively, are provided at proximal ends 28 and 40 arms 24 and 36, respectively, to facilitate moving arms 24 and 36 toward and away from each other.

While not specifically shown, first scissors half 12 and second scissors half 14 are formed of an electrically conductive material and are provided with an insulating material along substantially the length thereof to electrically isolate first scissors half 12 and second scissors half 14 and prevent shock to the surgeon and patient. For example, an electrically conductive material such as, for example, stainless steel may be used in forming first scissors half 12 and second scissors half 14. Electrically insulated material, such as, for example, polymers, ceramics, etc. may be used to electrically isolate substantially all of first scissors half 12 from second scissors half 14. A first electrical lead 46 is affixed to the conductive material of first arm 24 at proximal end 28 thereof. Likewise, the second electrical lead 48 is affixed near proximal end 40 of second arm 36. First and second electrical leads 46 and 48 may be integrally formed with first arm 24 and second arm 36 or may be removable therefrom. First and second electrical leads 46 and 48 are connectable to a remote electrical power supply (not shown) to energize bipolar scissors 10 and allow bipolar scissors 10 to cauterize tissue and form a hemostasis. In a particular embodiment, the remote electrical power supply is a radiofrequency or RF power supply.

Figure 2A:
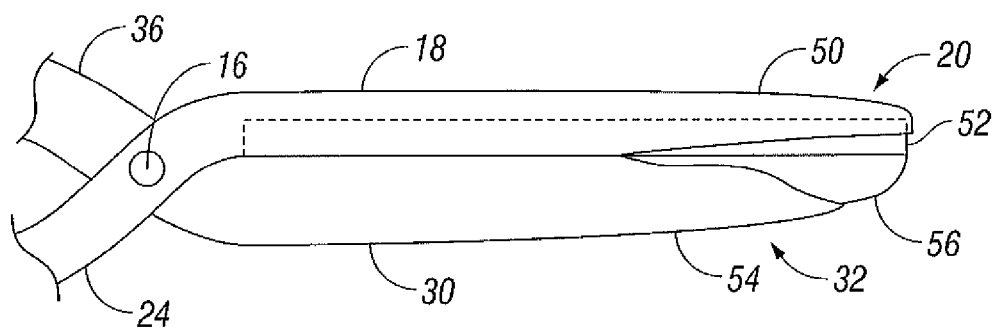
FIG. 2A a side view of the distal end of bipolar scissors with the jaws in the closed position.
Figure 2B:
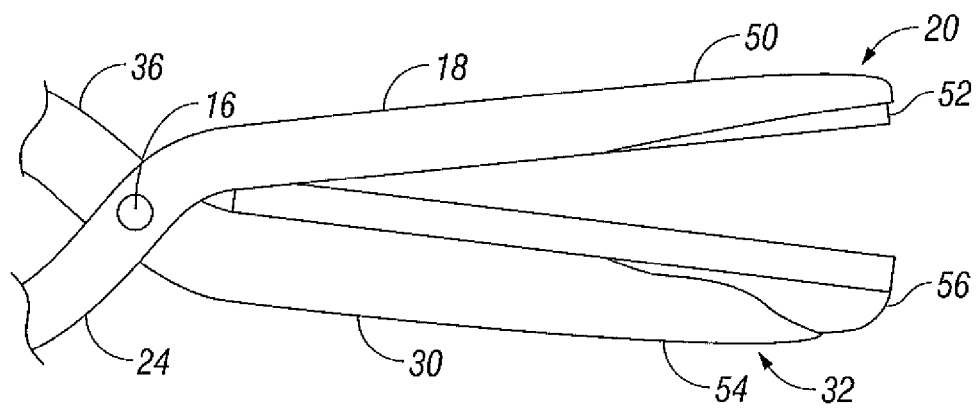
FIG. 2B is side view of the distal end of the bipolar scissors with the jaws in the open position.

Referring for the moment to FIGS. 1, 2A and 2B, in order to cut and cauterize tissue, while isolating nontarget tissues from the cauterizing energy source, first leg 18 includes a first electrically insulating outer portion 50 and a first electrically conductive portion 52. Likewise second leg 30 includes a second electrically insulating outer surface 54 and a second electrically conductive portion 56.

Figure 3A:
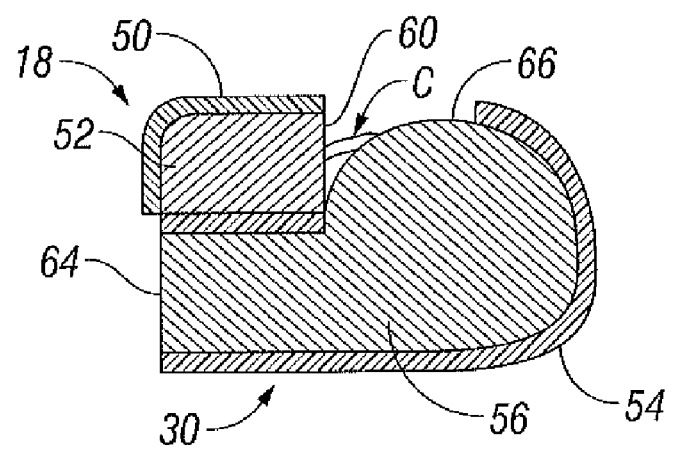
FIG. 3A is a cross-sectional view of the distal end of the bipolar scissors with the jaws in the closed position.
Figure 3B:
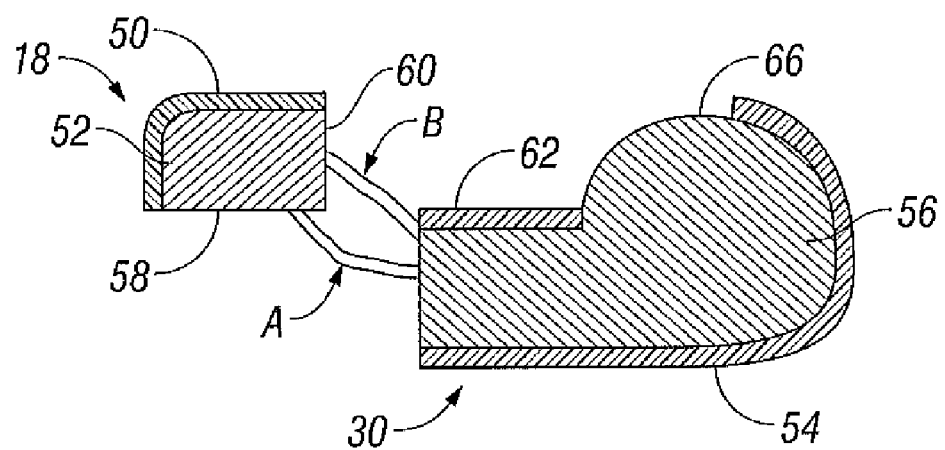
FIG. 3B is a cross-sectional view of the distal end of the bipolar scissors with the jaws in the open position.

Referring now to FIGS. 3A and 3B, details of first and second electrically conductive portions 52 and 56, along with the respective shearing surfaces of first and second legs 18 and 30, will now be described. First electrically conductive portion 52 of first leg 18 includes a first shearing surface 58 and a first side surface 60, both of which are electrically conductive. Second leg 30 includes a nonconductive shearing surface 62 that is formed on second electrically conductive portion 56 and cooperates with first shearing surface 58 to cut or excise tissue. Nonconductive second shearing surface 62 can be formed of any nonconductive materials, such as, for example, ceramics or other suitable nonconductive surfaces. Ceramics are particularly suitable materials for forming second shearing surface 62 in that ceramics are a relatively hard material and will retain their cutting ability throughout an extensive surgical operation. First shearing surface 58 on first leg 18 lies along substantially the same plane as nonconductive second shearing surface 62 on second leg 30 to allow a clean cut.

In one embodiment, to aid in hemostasis during specific surgical procedures, electrically conductive portion 56 includes a first electrically conductive surface 64 and a second electrically conductive surface 66. As shown, second electrically conductive surface 66 assumes a generally bulbous shape projecting away from electrically nonconductive second shearing surface 62.

As best shown in FIG. 3B, as first leg 18 and second leg 30 are moved together to initiate cutting of tissue, power or energy flux flows along lines A between first shearing surface 58 on first leg 18 and first electrically conductive surface 64 on second leg 30. Additionally, during the initial cutting of tissue, power or energy flux flows along lines B between first side surface 60 on leg 18 and first electrically conductive surface 64 on second leg 30. Depending upon the nature the tissue to be cut, and the rate at which the cut is made, more or less energy flux will follow along lines A or B.

As further shown in FIG. 3A, when first leg 18 and second leg 30 are moved to the fully closed cutting position, the geometry of second electrically conductive surface 66 brings second electrically conductive surface 66 into alignment with electrically conductive first side surface 60 on first leg 18 such that energy flux flows along line C (see also FIG. 5) between first side surface 60 on first leg 18 and second electrically conductive surface 66 on second leg 30. This allows bipolar scissors 10 to apply energy, and thus cause a hemostasis, to underlying tissues at the end of the cut or excision of tissue. Second electrically conductive surface 66 may have a bulbous shape as shown, or may be otherwise or similarly configured to facilitate a concentrated energy flux in conjunction with first side surface 60.

While not specifically shown, it should be noted that orientation of first shearing surface 58 on first leg 18 and nonconductive second shearing surface 62 on second leg 30 may eliminate the application of energy during the tissue cutting process.

Figure 4:
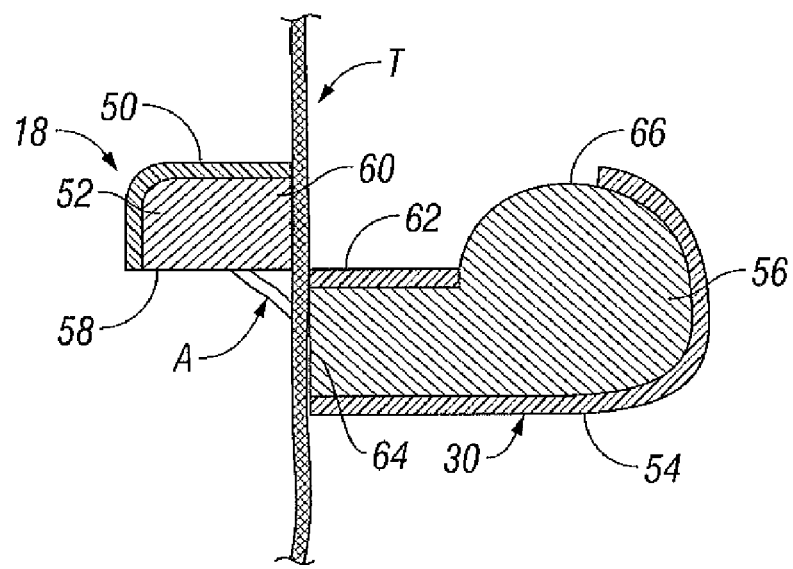
FIG. 4 is an end view illustrating the distal end of the bipolar scissors being used to transect a tissue plane.
Figure 5:
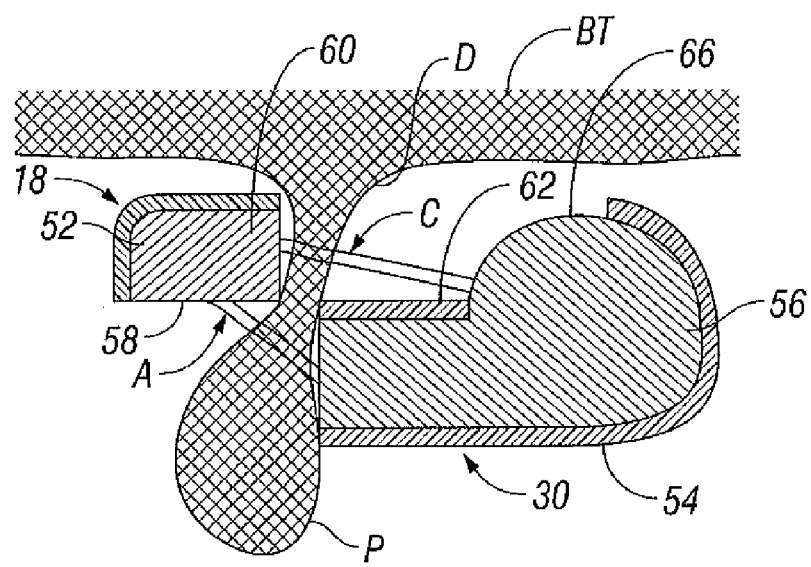
FIG. 5 is an end view illustrating the distal end of the bipolar scissors being use to excise a portion of tissue from a tissue bed.

Referring now to FIGS. 4 and 5, the use of bipolar scissors 10 to excise and cauterize various tissues will now be described. Referring initially the FIG. 4, the use of bipolar scissors 10 to transect and cauterize a tissue T is shown. Specifically, as first leg 18 is closed against second leg 30, first shearing surface 58 on first leg 18 cooperates with second shearing surface 62 on second leg 30 to cut or transect tissue T. As noted hereinabove, since the second shearing surface 62 is electrically nonconductive, no energy flux flows directly between first shearing surface 58 and second shearing surface 62 as the tissue is cut. However, during the initial cutting, energy flux may flow along lines A between first shearing surface 58 and first electrically conductive surface 64 to begin cauterizing the tissue during the initial cutting. Additionally, some small amount of energy flux may flow along lines B (FIG. 3B) to assist in cauterizing the cut ends of tissue T.

Referring now to FIG. 5, the use of bipolar scissors 10 to excise and cauterize tissue, such as, for example, adenoids, tonsils, or other projecting polyps will now be described. In these operations, a polyp P, for example, projects from an underlying fascia or muscle tissue BT. Initially, as first leg 18 is brought towards second leg 30 causing first shearing surface 58 to cooperate with second shearing surface 62, polyp P is excised and energy flux flows along lines A to cauterize polyp P. During and at the end of excising polyp P from underlying tissue BT, energy flux flows along lines C to cauterize underlying tissue BT at point D and help prevent any excess bleeding.

Figure 6:
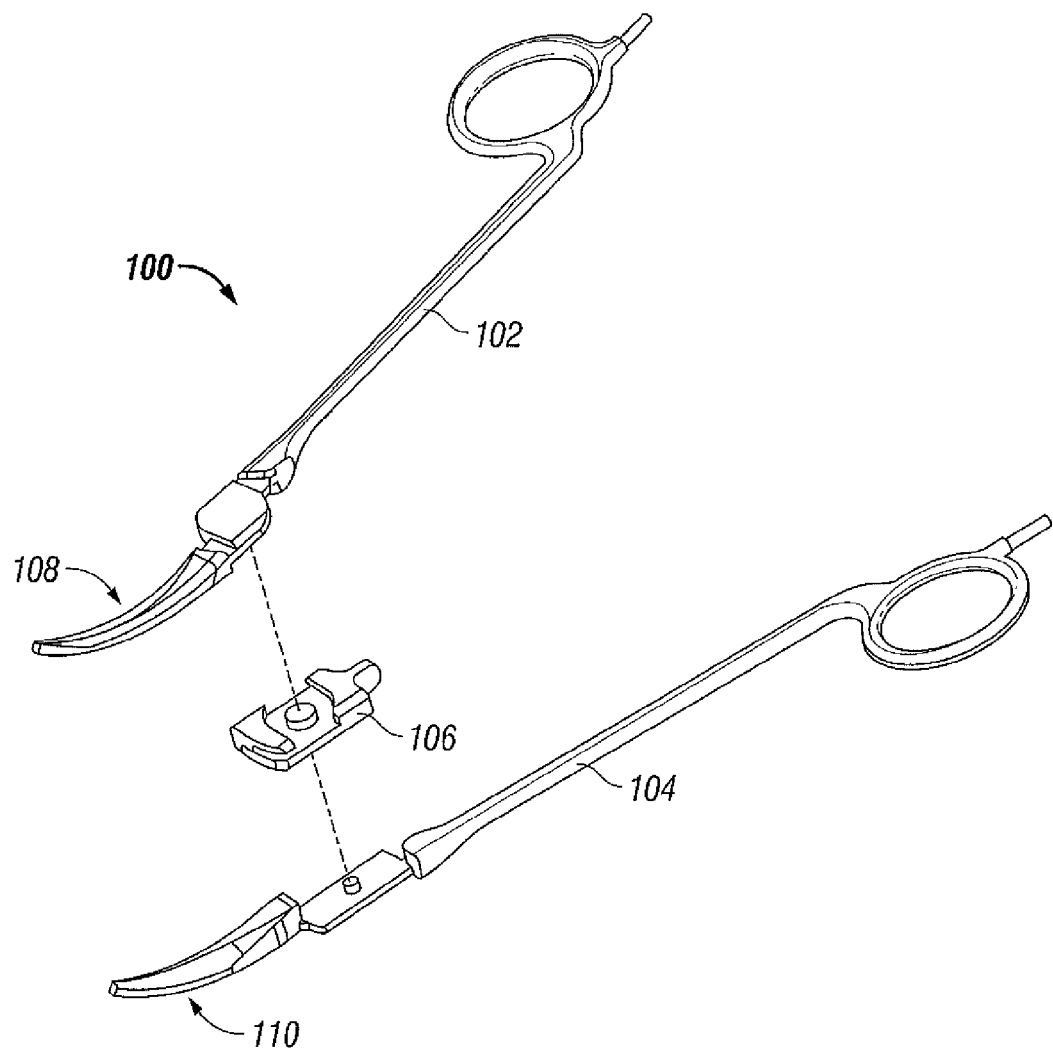
FIG. 6 is an assembly view of bipolar scissors in accordance with an embodiment of the present disclosure.
Figure 7:
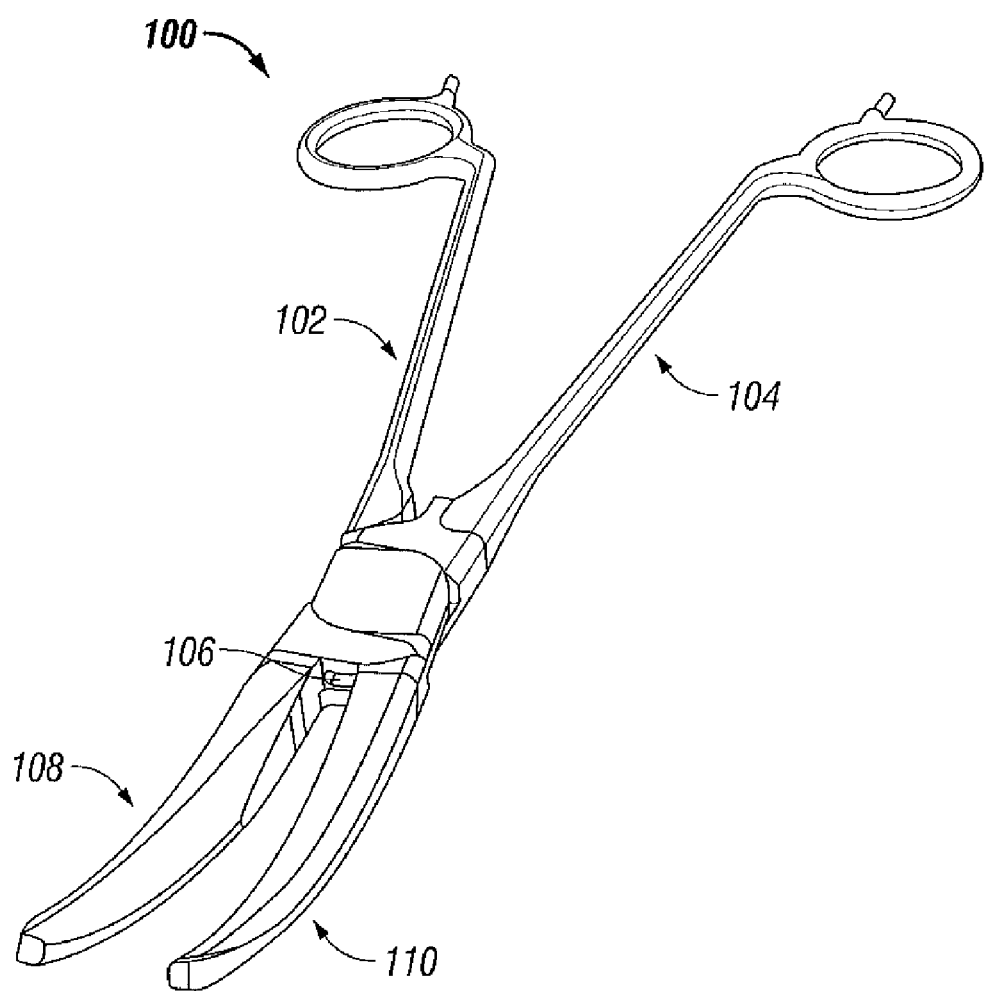
FIGS. 7 and 8 are perspective views of the bipolar scissors of FIG. 6.
Figure 8:
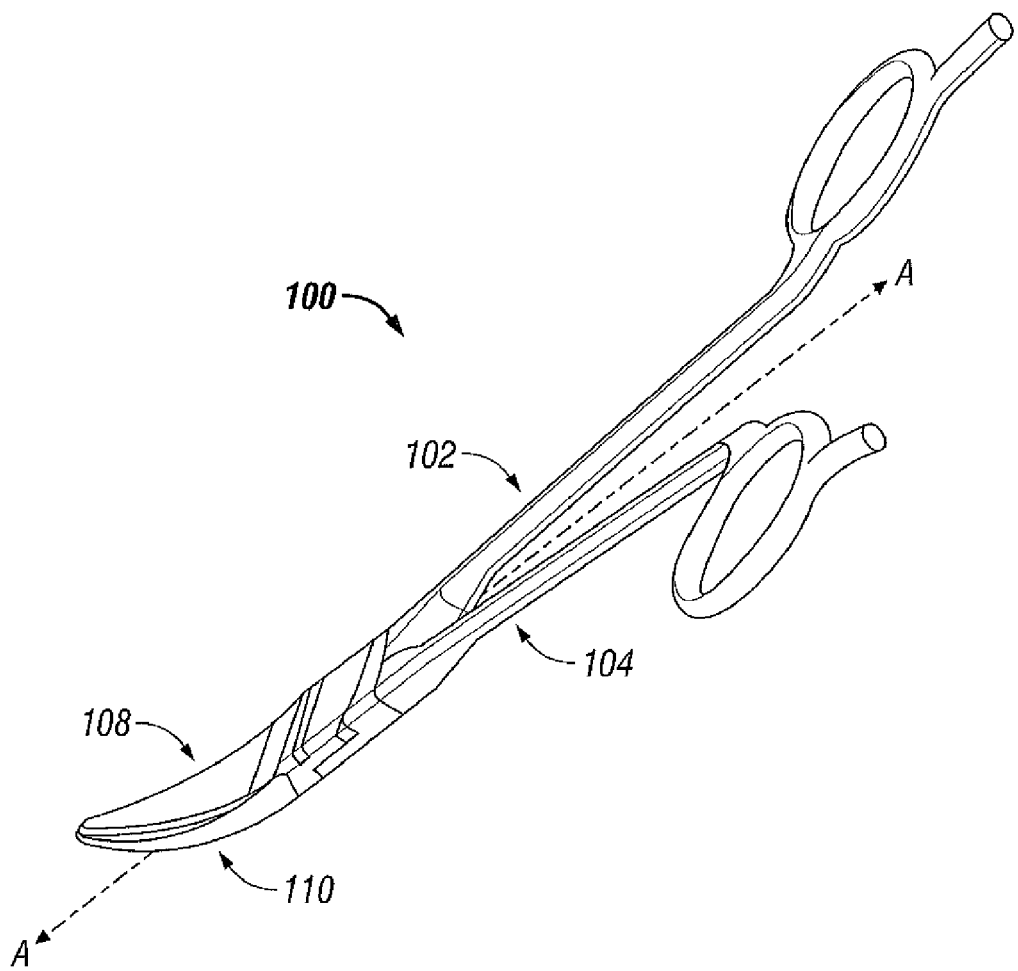

With reference to FIGS. 6-8, a bipolar scissors 100 is illustrated according to an embodiment of the present disclosure is illustrated. Bipolar scissors 100 includes a first scissors half 102 and a second scissors half 104. First and second scissors halves 102, 104 are pivotably movable relative to one another and are electrically isolated from one another via a non-conductive hinge 106. It is envisioned that bipolar scissors 100 includes features from bipolar scissors 10 of FIGS. 1-5, including second electrically conductive surface 66 assuming a generally bulbous shape that projects away from electrically nonconductive second shearing surface 62.

First scissors half 102 includes a first leg 108 disposed adjacent a distal end thereof and second scissors half 104 includes a second leg 110 disposed adjacent a distal end thereof. First leg 108 and second leg 110 are movable relative to one another between a spaced apart position (FIG. 7) and an approximated or closed position (FIG. 8), e.g., to cut and/or coagulate tissue.

In the embodiments illustrated in FIGS. 6-8, first leg 108 and second leg 110 include a curved or arcuate portion, e.g., for facilitating access to surgical sites. In addition to the curved portions of first and second legs 108, 110, first and second legs 108, 110 are shown curved away from a plane A-A defined by first and second scissors halves 102, 104. That is, first and second legs 108, 110 are each shown to be doubly curved. The double curvature of first and second legs 108, 110 of this embodiment may help facilitate access to various target tissue, such as an adenoid, for instance.

Various modifications may be made to the embodiments disclosed herein. For example, shapes other than bulbous may be used for the second electrically conductive surface on the second leg in order to bring the second electrically conductive surface into alignment with the first electrically conductive side surface on the second leg. Further, as noted hereinabove, various nonconductive materials other than ceramics may be used for the second shearing surface on the second leg. Additionally, the disclosed orientations of the distal ends of the disclosed bipolar surgical instrument, including the first and second legs, may be incorporated into an electrosurgical instrument other than an open surgery instrument, for example laparoscopic or endoscopic instruments. Therefore, the above description should not be construed as limiting, but merely as exemplifications of particular embodiments. Those skilled in the art will envision other modifications within the scope and spirit of the claims appended hereto.

The invention claimed is:

1. An electro surgical instrument comprising:
a first leg having a first leg conductive shearing surface and a first leg conductive side surface;
a second leg movably mounted to the first leg, the first leg and second leg movable between an open position and a closed position, the second leg having a second leg nonconductive shearing surface, a second leg first conductive surface, and a second leg second conductive surface, wherein contacting portions of the first leg conductive shearing surface and the second leg non-conductive shearing surface define an imaginary shearing plane, the imaginary shearing plane extending beyond the contacting portions substantially parallel to at least one of the second leg non-conductive shearing surface or the first leg conductive shearing surface, wherein the second leg second conductive surface extends at least partially from the second leg into the imaginary shearing plane; and
wherein at least one of the first leg conductive side surface or the first leg conductive shearing surface is configured to be in selective electrical communication with the second leg first conductive surface as the first and second legs are moved toward the closed position, wherein the first leg conductive side surface is in selective electrical communication with the second leg second conductive surface when the first leg conductive shearing surface and the second leg non-conductive shearing surface are contacting.

2. The electrosurgical instrument as recited in claim 1, wherein the first and second legs are pivotally mounted for movement at a pin, the pin electrically isolating the first leg from the second leg.

3. The electrosurgical instrument as recited in claim 2, wherein the first leg has a first arm extending proximally from the pin.

4. The electrosurgical instrument as recited in claim 3, wherein the second leg has a second arm extending proximally from the pin.

5. The electrosurgical instrument as recited in claim 4, wherein the first and second arms each have an electrical connection at a proximal end thereof for connection to an electrical power source.

6. The electrosurgical instrument as recited in claim 5, wherein the electrical power source is an RF power source.

7. The electrosurgical instrument as recited in claim 4, wherein at least one of the first and second arms has a finger ring adjacent a proximal end thereof.

8. The electrosurgical instrument as recited in claim 1, wherein the second leg second conductive surface is insulated from the first conductive surface.

9. The electrosurgical instrument as recited in claim 8, wherein the second leg second conductive surface is in electrical communication with the first leg conductive side surface in the closed position.

10. The electrosurgical instrument as recited in claim 8, wherein the second leg first conductive surface is in electrical communication with the first leg conductive side surface or the first leg conductive shearing surface as the first leg is moved toward the second leg to cut tissue.

11. The electrosurgical instrument as recited in claim 8, wherein the first leg conductive side surface lies along a common plane with the second leg first conductive surface of the second leg.

12. The electro surgical instrument as recited in claim 1, wherein the first leg conductive shearing surface cooperates with the second leg non-conductive shearing surface to cut tissue.

13. The electrosurgical instrument as recited in claim 1, wherein the first leg includes an electrically insulated outer surface disposed on at least a portion of the first leg.

14. The electrosurgical instrument as recited in claim 1, wherein the second leg includes an electrically insulated outer surface disposed on at least a portion of the second leg.

15. The electrosurgical instrument as recited in claim 1, wherein the second leg non-conductive shearing surface is formed of a ceramic.

16. The electrosurgical instrument as recited in claim 1, wherein the second leg second conductive surface includes a bulbous shape.

17. A method for performing a surgical function, comprising:
providing an electrosurgical instrument, including:
a first leg having a first leg conductive shearing surface and a first leg conductive side surface; a second leg movably mounted to the first leg, the first leg and second leg movable between an open position and a closed position, the second leg having a second leg non-conductive shearing surface, a second leg first conductive surface, and a second leg second conductive surface, wherein contacting portions of the first leg conductive shearing surface and the second leg non-conductive shearing surface define an imaginary shearing plane, the imaginary shearing plane extending beyond the contacting portions substantially parallel to at least one of the second leg non-conductive shearing surface or the first leg conductive shearing surface, wherein the second leg second conductive surface extends at least partially from the second leg into the imaginary shearing plane; and
wherein at least one of the first leg conductive side surface or the first leg conductive shearing surface is configured to be in selective electrical communication with the second leg first conductive surface as the first and second legs are moved toward the closed position, wherein the first leg conductive side surface is in selective electrical communication with the second leg second conductive surface when the first leg conductive shearing surface and the second leg non-conductive shearing surface are contacting;
positioning the electrosurgical instrument adjacent target tissue; and
moving at least one of the first leg and the second leg toward the other to sever the target tissue disposed therebetween.

18. The method of claim 17, further including the step of:
activating a source of electrosurgical energy to coagulate tissue adjacent the first leg and the second leg.

19. The method of claim 18, wherein the second leg second conductive surface includes a bulbous shape.

20. The method of claim 18, wherein activating the source of electrosurgical energy causes electrosurgical energy to move between the first leg conductive side surface and the second leg second conductive surface.

* * * * *